United States Patent [19]

Ueda et al.

[11] Patent Number: 5,169,820

[45] Date of Patent: Dec. 8, 1992

[54] CATALYST FOR PRODUCING PHTHALIC ANHYDRIDE

[75] Inventors: Kenji Ueda; Tatsuya Kawabata; Masaaki Okuno, all of Hyogo; Chisako Nishio, Kanagawa; Shinya Tanaka, Hyogo, all of Japan

[73] Assignee: Nippon Shokubai Kagaku Kogyo Co., Ltd., Osaka, Japan

[21] Appl. No.: 665,063

[22] Filed: Mar. 6, 1991

[30] Foreign Application Priority Data

Mar. 16, 1990 [JP] Japan ................................ 2-63975

[51] Int. Cl.$^5$ ..................... B01J 21/06; B01J 23/04; B01J 23/22; B01J 23/50
[52] U.S. Cl. .................................. 502/209; 502/347; 502/348
[58] Field of Search ............... 502/209, 347, 348, 248, 502/249

[56] References Cited

U.S. PATENT DOCUMENTS

| | | | |
|---|---|---|---|
| 3,232,955 | 2/1966 | Nonnenmacher et al. | 502/209 X |
| 3,843,552 | 10/1974 | Jouy et al. | 252/432 |
| 3,909,457 | 9/1975 | Friedrichsen et al. | 252/476 |
| 4,046,780 | 9/1977 | Nakanishi et al. | 260/346.4 |
| 4,356,112 | 10/1982 | Nakanishi et al. | 252/435 |
| 4,481,304 | 11/1984 | Sato et al. | 502/209 |

FOREIGN PATENT DOCUMENTS

| | | |
|---|---|---|
| 017865 | 10/1980 | European Pat. Off. . |
| 037492 | 10/1981 | European Pat. Off. . |
| 1203321 | 8/1970 | United Kingdom . |

OTHER PUBLICATIONS

Japanese Patent Publication 47-15323 (Japanese Official Patent Gazette of Shows 47-15323) with translation of p. 1 from lines 28-35 of column 1.
Japanese Patent Publication 49-41036 (Japanese Official Patent Gazette of Shows 49-41036) with translation of p. 1 from lines 26-35 of column 1.
Japanese Patent Publication 52-4538 (Japanese Official Patent Gazette of Shows 53-4538) with translation of p. 1, from line 17 of column 1 to line 6 of column 2.
Japanese Laid-open Patent 47-5661 (Japanese Official Patent Provisions Publication of Shows 47-5661) with translation of p. 1, line 4 of left column to line 6 of right column; p. 2, from line 15 from line 15 of a left column to line 1 of right column in lower hals.
Japanese Laid-open Patent 49-89694 (Japanese Official Patent Provisional Publication of Shows 49-89694) with translation of p. 1, line 5-15 and p. 2, line 16 of R column on line 2 of L column.
Japanese Patent Publication 59-1378 (Japanese Official Patent Gazette of Shows 59-1378) with translation of p. 1, line 19-35 of column 1.
Chemical Abstract No. 67(9): 43560h dated Aug. 28, 1967.
Chemical Abstract No. 68(25): 117462x dated Jun. 17, 1968.
Chemical Abstract No. 78(15): 97384z dated Apr. 6, 1973.
Chemical Abstract No. 86(26): 195651u dated Jun. 27, 1977.
Chemical Abstract No. 90(7): 5462h dated Feb. 12, 1979.

*Primary Examiner*—W. J. Shine
*Attorney, Agent, or Firm*—Lowe, Price, LeBlanc & Becker

[57] ABSTRACT

The invention presents catalysts for producing phthalic anhydride by vapor phase catalytic oxidation of ortho-xylene and/or naphthalene with molecular oxygen or gas containing molecular oxygen. The catalyst is prepared by supporting a catalytic active substance comprising 1 to 20 parts by weight (hereinafter abbreviated "parts") of vanadium oxide as $V_2O_3$, 99 to 80 parts of anatase type titanium dioxide with specific surface area of 10 to 60 m$^2$/g as $TiO_2$ and per 100 parts of the sum of these two ingredients, 0.05 to 1.2 parts of at least one element selected from potassium, cesium, rubidium and thallium as oxide, and 0.05 to 2 parts of silver as $Ag_2O$ on a heat resistant inorganic carrier. The catalyst may also contain, per 100 parts in total of vanadium oxide and titanium dioxide, 0 to 1 part of niobium as $Nb_2O_5$, 0 to 1.2 parts of phosphorus as $P_2O_3$, and 0 to 5 parts of antimony as $Sb_2O_3$ (however, contents of niobium, phosphorus and antimony will not be zero at the same time).

3 Claims, No Drawings

CATALYST FOR PRODUCING PHTHALIC ANHYDRIDE

BACKGROUND OF THE INVENTION

The present invention relates to a catalyst for producing phthalic anhydride, and more particularly to a catalyst for producing phthalic anhydride by vapor phase catalytic oxidation of orthoxylene and/or naphthalane with molecular oxygen or gas containing molecular oxygen.

Catalysts for producing phthalic anhydride having a catalytic active substance mainly composed of vanadium oxide and titanium oxide supported on an inert carrier are widely known, and are disclosed, for example, in the Japanese Patent Publications 47-15323, 49-41036, 52-4538, and the Japanese Laid-open Patents 47-5661, 49-89694. These catalysts have their own features, and some of them are used industrially and achieving due results.

There is, however, an ample room for improvement of the catalyst performance, and regarding the selectivity to begin with, an increase of yield by only one percent is notable in its economical effect considering the scale of the producing equipment. Furthermore, improvement of selectivity makes it easier to operate for heat treatment and distillation until the products are obtained, and with the improvement of selectivity it is simultaneously expected to have an effect of producing products of high quality at low cost. Such improvement of selectivity is also important for using the raw materials effectively.

What is also important is the improvement of productivity and the maintenance of stable production by retaining the catalyst activity. One of the methods for enhancing the productivity is to perform oxidation reaction in high load reaction conditions by, for example, raising the material gas concentration. However, the reaction of obtaining phthalic anhydride from orthoxylene or naphthalene is accompanied by a violent heat generation, and the temperature rise in the hot spot area in high concentration condition is extreme, and an excessive oxidation reaction is produced, and the yield of the phthalic anhydride is lowered, while deterioration of the catalyst is extremely promoted.

Catalysts capable of withstanding such high load reaction conditions have been already proposed, for example, by the present applicant in the Japanese Patent Publication 59-1378.

SUMMARY OF THE INVENTION

The invention is intended to present a catalyst favorably used in production of phthalic anhydride, having the catalytic performance improved markedly as compared with the conventional catalyst.

It is hence a primary object of the invention to present a catalyst for producing phthalic anhydride capable of producing phthalic anhydride at a high selectivity by vapor phase catalytic oxidation of orthoxylene and/or naphthalene.

It is other object of the invention to present a catalyst for producing phthalic anhydride capable of producing phthalic anhydride stably, excellent in durability and small in lowering of catalytic activity by long-term use, being a catalyst for producing phthalic anhydride by vapor phase catalytic oxidation of orthoxylene and/or naphthalene.

It is a further object of the invention to present a catalyst for producing phthalic anhydride capable of producing phthalic anhydride stably for a long period, capable of manufacturing phthalic anhydride at high selectively even in high load reaction condition and excellent in durability, in production of phthalic anhydride by vapor phase catalytic oxidation of orthoxylene and/or naphthalene.

The present inventors, as a result of intensive researches, found that the above objects could be achieved by introducing silver as a component of catalytic active substance into the vanadium-titanium catalyst, and reached this invention on the basis of this finding.

More specifically, the invention relates to a catalyst for producing phthalic anhydride by vapor phase catalytic oxidation of orthoxylene and/or naphthalene with molecular oxygen or gas containing molecular oxygen, having a catalytic active substance comprising 1 to 20 parts by weight of vanadium oxide as $V_2O_5$, 99 to 80 parts by weight of anatase type titanium dioxide with specific surface area of 10 to 60 $m^2/g$ as $TiO_2$, and per 100 parts by weight in the total of the above two components, 0.05 to 1.2 parts by weight of at least one element selected from potassium, cesium, rubidium and thallium as an oxide, and 0.05 to 2 parts by weight of silver as $Ag_2O$, supported on a heat resistant inorganic carrier (hereinafter this is called catalyst 1).

The invention moreover relates to a catalyst for producing phthalic anhydride by vapor phase catalytic oxidation of orthoxylene and/or naphthalene with molecular oxygen or gas containing molecular oxygen, having a catalytic active substance comprising 1 to 20 parts by weight of vanadium as $V_2O_5$, 99 to 80 parts by weight of anatase type titanium dioxide with specific surface area of 10 to 60 $m^2/g$ as $TiO_2$, and per 100 parts by weight in the total of the above two components, 0 to 1 part by weight of niobium as $Nb_2O_5$, 0.05 to 1.2 parts by weight of at least one element selected from potassium, cesium, rubidium and thallium as oxide, 0 to 1.2 parts by weight of phosphorus as $P_2O_5$, 0 to 5 parts by weight of antimony as $Sb_2O_3$, and 0.05 to 2 parts by weight of silver as $Ag_2O$ (where contents of niobium, phosphorus and antimony will not be zero at the same time), supported on a heat resistant inorganic carrier (this is called hereinafter catalyst 2).

The invention is described in further detail below.

It is one of the features of the invention that anatase type titanium dioxide with specific surface area of 10 to 60 $m^2/g$, preferably 15 to 40 $m^2/g$, is used as a component of the catalytic active substance.

If the specific surface area of the anatase type titanium dioxide is less than 10 $m^2/g$, the activity of the obtained catalyst is low, or when exceeding 60 $m^2/g$, the durability of the catalyst is worsened, and the yield is lowered in a short time, which is not preferable.

In the invention, among the anatase type titanium dioxide defined above, the material with the mean particle size of 0.4 to 0.7 μm or preferably 0.45 to 0.60 μm, and substantially in a spherical form is used favorably in particular.

The anatase type titanium dioxide used favorably in the invention is manufactured by a method called sulfuric acid solution method, and is high in mechanical strength in spite of porosity, and possesses the strength so high as to be regarded as "primary particles" not crushed by mechanical grinding by an ordinary ball mill or the like. Although this anatase type titanium oxide has a large mean particle size in a range of 0.4 to 0.7 μm, it has a high specific surface area of 10 to 60 m²/g, and it is essentially an assembly of primary particles having a small diameter. Therefore, this anatase type titanium dioxide is not required to be true spheres, but it may be enough if it is spherical substantially.

According to the sulfuric acid solution method, ilmenite ($FeOTiO_2$) is treated with sulfuric acid at a lower concentration than in production of titanium dioxide by sulfuric acid solidification method, usually with sulfuric acid at about 70 to 80% to obtain titanium sulfate, and this titanium sulfate is hydrolyzed under pressure at 150° to 180° C., and is further baked at 600° to 900° C. to obtain anatase type titanium oxide. This anatase type titanium oxide may contain, due to the material ores, iron, zinc, aluminum, manganese, chromium, calcium or lead, but it does not matter particularly if the oxide contents in titanium oxide are not more than 0.5 wt. %, from the viewpoint of catalytic performance.

The heat resistant inorganic carrier used in the invention is required to be stable for a long period at a temperature sufficiently higher than the catalyst temperature when producing phthalic anhydride as well as baking temperature of catalyst, and not to react with catalytic active substance.

Examples of such heat resistant inorganic carrier may include, among others, silicon carbide (SiC), alumina, zirconium oxide, and titanium oxide. Particularly preferable among them is the silicon carbide carrier with the alumina ($Al_2O_3$) content of 20 wt. % or less, preferably 5 wt. % or less, and apparent porosity of 10% or more, preferably 15 to 45%. In particular, the silicon carbide carrier with the alumina content of 5 wt. % or less, silicon carbide content of 95 wt. % or more, and apparent porosity of 15 to 45% is favorably used. More favorably, the silicon carbide carrier obtained by self-sintering of powder of silicon carbide with purity of 98% or more is preferred.

The shape of the heat resistant inorganic carrier is not particularly limited, but spherical or columnar shape is easy to handle, and the mean diameter of about 2 to 15 mm is preferred.

Catalyst 1 of the invention is obtained by supporting, on this heat resistant inorganic carrier, a catalytic active ingredient comprising 1 to 20 parts by weight of vanadium oxide as $V_2O_5$, 99 to 80 parts by weight of anatase type titanium oxide as $TiO_2$, and per 100 parts by weight of the sum of these two ingredients, 0.05 to 1.2 parts by weight of at least one element selected from potassium, cesium, rubidium and thallium as oxide, and 0.05 to 2 parts by weight of silver as $Ag_2O$.

It is one of the features of the invention, as mentioned hereabove, that silver is introduced as an ingredient of the catalytic active substance, and the silver content in catalyst 1 is to 0.05 to 2 parts by weight as $Ag_2O$, or preferably 0.1 to 1 part by weight. The objects of the invention will not be achieved if the silver content is too much or too less. In other words, if the silver content as $Ag_2O$ is less than 0.05 part by weight, the effect of improving the performance by addition of silver is lowered. If the silver content exceeds 2 parts by weight, adverse effects are brought about to the catalyst performance, and the selectivity of phthalic anhydride is lowered.

Catalyst 2 of the invention is obtained by supporting, on the heat resistant inorganic carrier, a catalyst active ingredient comprising 1 to 20 parts by weight of vanadium oxide as $V_2O_5$, 99 to 80 parts by weight of anatase type titanium oxide as $TiO_2$, and per 100 parts by weight of the total of these two ingredients, 0 to 1 part by weight of niobium as $Nb_2O_5$, 0.05 to 1.2 parts by weight of at least one element selected from potassium, cesium, rubidium and thallium as oxide, 0 to 1.2 parts by weight of phosphorus as $P_2O_5$, 0 to 5 parts by weight of antimony as $Sb_2O_3$, and 0.05 to 2 parts by weight of silver as $Ag_2O$ (where contents of niobium, phosphorus and antimony will not be zero at the same time).

In catalyst 2, same as in catalyst 1, the silver content is 0.05 to 2 parts by weight as $Ag_2O$, or preferably 0.1 to 1 part by weight. The objects of the invention will not be achieved if the silver content is too much or too less.

Besides, in catalyst 2, the catalyst supporting, on the heat resistant inorganic carrier, the catalytic active ingredient comprising 0.01 to 1 part by weight of niobium as $Nb_2O_5$, 0.2 to 1.2 parts by weight of phosphorus as $P_2O_5$, and 0.5 to 5 parts by weight of antimony as $Sb_2O_3$ is particularly preferred because the selectivity of phthalic anhydride is enhanced.

The starting materials of vanadium, niobium, potassium, cesium, rubidium, thallium, phosphorus and antimony when preparing catalyst 1 and catalyst 2 may be properly selected from, aside from such oxides as $V_2O_5$, $Nb_2O_5$, $K_2O$, $Cs_2O$, $Rb_2O$, $Tl_2O$, $P_2O_5$ and $Sb_2O_3$, the compounds transformed to such Oxide by heating, such as ammonium salt, nitrate, sulfate, halide, organic acid salt and hydroxide of the individual elements.

As for the silver ingredient, aside from $Ag_2O$, nitrate, ammonium salt, sulfate, halide, organic acid salt, hydroxide, amine complex, phosphate and sulfide may be used. Some of them, such as silver halide and silver phosphate, are not transformed into oxide in the heating condition of production of catalyst, but all of them may be used in the invention without trouble. Besides, when silver phosphate is used, or when adding phosphorus ingredient as catalytic active substance, it is not necessary to consider the content of phosphorus in the silver phosphate, and it is all right as far as the content as the oxide of phosphorus ingredient is within the prescribed range.

The method of supporting the catalytic active substance on the heat resistant inorganic carrier in production of catalyst of the invention is not particularly limited, and it is possible to support by a general method. In particular, the simplest manner is to put a specific volume of carrier into a rotary drum which can be heated from outside, and spray the slurry containing the catalytic active substance while keeping it at 200° to 300° C. to support the catalytic active substance.

The supporting amount of the catalytic active substance on the heat resistant inorganic carrier varies with the carrier size, and it is generally 3 to 20 g per 100 cc of the carrier.

The catalytic active substance layer obtained by supporting the catalytic active substance on the carrier should preferably have such a surface characteristic as 50% or more of the total fine pore volume occupied by the fine pores having the diameter of 10 μm or less of the total fine pore volume occupied by fine pore having the diameter of 0.15 to 0.45 μm, and more preferably the surface characteristic of 75% or more of the total fine pore volume occupied by the fine pores with the diameter of 10 μm or less of the total fine pore volume occupied by the fine pores having the diameter of 0.15 to 0.45 μm.

By using the catalytic active layer having such surface characteristic, the object of the invention may be more effectively achieved.

The catalytic active substance layer having such surface characteristic may be easily formed by adjusting the slurry concentration depending on the particle size of the essential primary particles of the anatase type titanium oxide, in the supporting method using, for example, the rotary drum as mentioned above (see the Japanese Patent Publication 49-41036). Practically, when using anatase type titanium oxide with the primary particle size of 0.005 to 0.05 $\mu$m, the slurry concentration is defined to 5 to 25 wt. %, or preferably 10 to 20 wt. %, or when using anatase type titanium dioxide with the primary particle size of 0.05 $\mu$m greater, the slurry concentration is defined at 10 to 40 wt. %, or preferably 15 to 25 wt. %, so that the catalytic active substance layer having such surface characteristic as mentioned above may be formed.

In the invention, the fine pore volume was determined from the fine pore diameter distribution measured by mercury injection porosimeter. The specific surface area of anatase type titanium dioxide was measured by the BET method, and the mean diameter was measured by using a transmission electron microscope.

After thus supporting the catalytic active substance layer, the catalyst of the invention is obtained by baking for 2 to 10 hours while passing air at a temperature of 450° to 700° C., or preferably 500° to 600° C.

The oxidation reaction of orthoxylene and/or naphthalene using the catalyst of the invention may be executed in the ordinary reaction condition. For example, a reaction tube with the inside diameter of 5 to 40 mm, or preferably 15 to 27 mm, is filled with the catalyst in a height of 1 to 5 m, or preferably 1.5 to 3 m, and this reaction tube is held at a temperature of 300° to 400° C., or preferably 330° to 380° C. by the heat medium, and in this reaction tube the material orthoxylene and/or naphthalene is blown, together with air or gas containing 5 to 21 vol. % molecular oxygen, at a rate of 5 to 70 g/Nm$^3$ (air) in the case of air, or 5 to 110 g/Nm$^3$ (gas containing molecular oxygen) in the case of gas containing molecular oxygen, at a spatial velocity of 1,000 to 6,000 hr$^{-1}$ (STP), or preferably 1,000 to 4,000 hr$^{-1}$ (STP).

In the above oxidation reaction, by dividing the catalyst layer in the reaction tube in two or more layers to dispose a plurality of reaction bands, and a plurality of catalysts controlled in the catalytic activity are disposed in these reaction bands so that the activity may be higher from the inlet toward the outlet of the material gas feed port in the reaction tube, so that the catalyst of the invention may be utilized advantageously.

Describing further by reference to an example of catalyst 2 of the invention, first the reaction tube is divided into two layers, and the inlet part is filled with specified catalyst (prestage catalyst) to a layer height of 30 to 70% of the overall catalyst layer height, while the remaining layer height at the outlet is filled with the catalyst (poststage catalyst) higher in activity than the prestage catalyst. The catalyst same in the catalytic composition but different in activity may be easily prepared by changing the content of, for example, phosphorus. Practically, by using 0.2 to 0.4 part by weight of phosphorus content as oxide, the prestage catalyst is prepared, and by using 0.4 to 1.2 parts by weight, the poststage catalyst higher in activity than the prestage catalyst may be prepared. The catalyst activity may be also controlled by changing the type and/or content of the element selected from potassium, cesium, rubidium and thallium.

By performing oxidation reaction in such condition as mentioned above, heat accumulation in the hot spot in the catalyst layer is suppressed, and deterioration of catalyst due to thermal load is prevented, so that a stable operation may be executed for a long term industrially. Besides, the excessive oxidation reaction by the hot spot is prevented, and various effects are obtained, including improvement of selectivity. Such effects are particularly notable in the high load reaction condition such as elevation of material gas, and the productivity may be markedly enhanced by raising the concentration of orthoxylene or naphthalene.

By using the catalysts of the invention, phthalic anhydride may be manufactured at high selectivity from orthoxylene and/or naphthalene. Therefore, the operations for heat treatment and distillation until obtaining products of phthalic anhydride are easy, and products of higher quality may be obtained at lower cost as compared with the conventional method.

The catalysts of the invention are excellent in durability, and accordingly long-term stable operation is possible industrially.

The catalysts of the invention produce phthalic anhydride at high selectivity even in the high load reaction condition by raising the concentration of material gas or the like, and are excellent in durability if used for a long period, so that the productivity of manufacture of phthalic anhydride may be notably enhanced by using the catalysts of the invention.

Therefore, the catalysts of the invention are extremely useful for manufacture of phthalic anhydride.

DETAILED DESCRIPTION OF THE PREFERRED EMBODIMENTS

The invention is further described below while referring to some of the preferred embodiments.

EXAMPLE 1

Preparation of Catalyst

Mixing 80% concentrated sulfuric acid to ilmenite and reacting sufficiently, an aqueous solution of titanium sulfate was obtained by diluting in water. Iron pieces were added to this as reducing agent, and the iron contents in ilmenite was reduced to ferrous ions, and cooled, and ferrous sulfate was precipitated and separated. To thus obtained aqueous solution of titanium sulfate, steam heated to 150° C. was blown, and hydrous titanium oxide was settled. It was washed in water, pickled and washed again in water, and was baked at 800° C. for 4 hours while passing air flow. It was crushed by jet air stream to obtain anatase type titanium oxide (hereinafter called sometimes simply as titanium dioxide) with the mean particle size of about 0.5 $\mu$m and specific surface area of 22 m$^2$/g.

To 6,400 cc of deionized water, 200 g of oxalic acid was dissolved to prepare aqueous solution of oxalic acid, and 47.25 g of ammonium metavanadate, 5.98 g of ammonium dihydrogen phosphate, 18.79 g of niobium chloride, 5.90 g of cesium sulfate, 5.39 g of silver nitrate, and 36.73 g of antimony trioxide were added and stirred sufficiently. To thus obtained solution, 1,800 g of titanium dioxide was added, and was stirred by emulsifying machine to prepare a catalyst slurry solution.

In a stainless steel rotary furnace of 35 cm in diameter and 80 cm in length which can be heated from outside, 2,000 cc of SiC self-sintered carrier of spherical form with diameter of 6 mm and apparent porosity of 35% was charged, and while rotating the furnace by preheating to 200° to 250° C., the catalyst slurry solution was sprayed on the carrier, and the catalytic active substance was supported at a rate of 8 g/100 cc (carrier). Afterwards, while passing air, it was baked in an electric oven for 6 hours at 580° C., and catalyst A was prepared.

Table 1 shows the composition of catalyst A, the rate (vol. %) of the total fine pore volume occupied by fine pores with diameter of 0.15 to 0.45 μm to the total fine pore volume occupied by fine pores with 10 μm or less in the catalytic active substance layer, and the specific surface area and mean particle size of the titanium dioxide used in preparation of catalyst (these are collectively called catalyst characteristics hereinafter).

Meanwhile, the rate of the volume occupied by fine particles with 0.15 to 0.45 μm to the total fine pore volume was determined from the result of measurement of fine pore distribution by mercury injection porosimeter.

Catalyst B was prepared in the same manner as in preparation of catalyst A, except that the content of ammonium dihydrogen phosphate was changed to 23.92 g.

The catalyst characteristics of catalyst B are shown in Table 1.

The phosphorus content in catalyst B was higher than that in catalyst A, and the activity of catalyst B was higher than that of catalyst A.

Oxidation Reaction

In an iron-made reaction tube of 25 mm in inside diameter and 3 m in length immersed in a molten salt bath kept at 355° C., first the catalyst B was charged as poststage catalyst in a height of 1 m at the material gas outlet part, then the catalyst A as prestage catalyst in a height of 1.5 m at the inlet part.

Orthoxylene was mixed at a rate of 85 g/Nm$^3$ (synthetic gas) to a synthetic gas comprising 10 vol. % of oxygen, 10 vol. % of steam and 80 vol. % of nitrogen, and this mixture gas was led into the upper inlet of the reaction tube at a space velocity (SV) of 2,500 hr$^{-1}$ (STP) to perform oxidation reaction of orthoxylene.

At the beginning of reaction, 3 months after start of reaction and 6 months after start of reaction, the yield of phthalic anhydride was measured, and the results are shown in Table 2. Meanwhile, the conversion rate of orthoxylene is nearly 100%, and this yield can be regarded as the selectivity of phthalic anhydride.

EXAMPLE 2

Catalyst C and catalyst D were prepared in the same manner as in Example 1 except that 4.94 g of silver sulfate was used, instead of 5.39 g of silver nitrate in Example 1, and the oxidation reaction was conducted in the same procedure as in Example 1.

The catalyst characteristics of catalysts C, D are shown in Table 1, and results of oxidation reaction in Table 2.

EXAMPLE 3

Catalyst E and catalyst F were prepared in the same manner as in Example 1, except that 4.42 g of silver phosphate was used instead of 5.39 g of silver nitrate in Example 1, and the oxidation reaction was conducted in the same procedure as in Example 1.

The catalyst characteristics of catalysts E, F are shown in Table 1, and results of oxidation reaction in Table 2.

Reference 1

Catalysts K, L were prepared in the same manner as in Example 1, except that the content of cesium sulfate was 8.25 g and that silver was not added, and the oxidation reaction was conducted in the same procedure as in Example 1.

The catalyst characteristics of catalysts K, L are shown in Table 1, and results of oxidation reaction in Table 2.

EXAMPLE 4

Preparation of Catalyst

To ilmenite, 80% concentrated sulfuric acid was mixed and allowed to react sufficiently, then the product was diluted to obtain aqueous solution of titanium sulfate. Iron pieces were added to it as reducing agent, and the iron content in ilmenite was reduced to ferrous ions, and cooled, and ferrous sulfate was precipitated and separated. To thus obtained aqueous solution of titanium sulfate, steam heated to 1 50° C. was blown, and hydrous titanium oxide was settled. It was washed in water, pickled, and washed again in water, and was baked at 700° C. for 4 hours while passing air flow. It was crushed by jet air stream, and anatase type titanium dioxide with specific surface area of 33 m$^2$/g measured by BET method at mean particle size of about 0.45 μm was obtained.

To 6,400 cc of deionized water, 900 g of oxalic acid was dissolved to obtain aqueous solution of oxalic acid, and in this aqueous solution 408.60 g ammonium metavanadate, 10.34 g of ammonium dihydrogen phosphate, 17.33 g of niobium chloride, 2.72 g of cesium sulfate, 3.92 g of potassium sulfate, 31.05 g of silver nitrate, and 42.35 g of antimony trioxide were added, and sufficiently stirred. To thus obtained solution, 1,800 g of titanium dioxide was added, and the mixture was stirred by emulsifying machine to prepare a catalyst slurry.

Using this slurry, the catalytic active substance was supported in the same manner as in Example 1. The supporting rate was 8.0 g/100 cc (carrier).

Afterwards, while passing air, it was baked in an electric oven at 560° C. for 6 hours to prepare catalyst G.

Catalyst H was prepared in the same manner as in preparation of catalyst G, except that the content of ammonium dihydrogen phosphate was 31.02 g.

Oxidation Reaction

In an iron-made reaction tube of 25 mm in inside diameter and 3 m in length immersed in a molten salt bath kept at 365° C., first catalyst H was charged as poststage catalyst to a height of 1 m, then catalyst G as prestage catalyst to a height of 1.5 m, and from the upper part of the reaction tube naphthalene is mixed at a rate of 85 g/Nm$^3$ (synthetic gas) to a synthetic gas comprising 10 vol. % of oxygen, 10 vol. % of steam and 80 vol. % of nitrogen, and this mixed gas was introduced at a space velocity of 2,500 hr$^{-1}$ (STP) to perform oxidation reaction.

The catalyst characteristics of catalysts G, H are shown in Table 1, and results of oxidation reaction in Table 2.

Reference 2

Catalysts M, N were prepared in the same manner as in preparation of catalysts G, H in Example 4, except that the content of potassium sulfate was 1.96 and that the content of silver nitrate was 77.63 g, and the oxidation reaction was performed in the same procedure as in Example 4.

The catalyst characteristics of catalysts M, N are shown in Table 1, and results of oxidation reaction in Table 2.

EXAMPLE 5

Preparation of Catalyst

To 6,400 cc of deionized water, 200 g of oxalic acid was dissolved to prepare aqueous solution of oxalic acid, and to this aqueous solution 96.48 g of ammonium metavanadate, 4.82 g of cesium sulfate, 1.18 g of thallium nitrate and 2.75 g of silver nitrate were added and stirred sufficiently. To thus obtained solution, the same anatase titanium dioxide as used in Example 1 was added by 1,800 g as $TiO_2$, and the mixture was stirred by emulsifying machine to obtain a slurry.

Using the slurry, the catalytic active substance was supported in the same manner as in Example 1. The supporting rate was 8.0 g/100 cc (carrier).

Then, while passing air, the mixture was baked in an electric oven at 550° C. for 6 hours to obtain catalyst I (prestage catalyst).

Catalyst J (poststage catalyst) was prepared in the same manner as in preparation of catalyst I, except that 2.96 g of rubidium nitrate was used instead of cesium sulfate and thallium nitrate.

Oxidation Reaction

Oxidation reaction was conducted in the same procedure as in Example 1, except that a mixed gas of mixing 70 g/$Nm^3$ (synthetic gas) of orthoxylene to a synthetic gas comprising 21 vol. % of oxygen and 79 vol. % of nitrogen was used as the material gas, and that this mixed gas was introduced from the upper inlet of the reaction tube at a space velocity of 3,000 $hr^{-1}$ (STP).

The catalyst characteristics of catalysts I, J are shown in Table 1, and results of oxidation reaction in Table 2.

EXAMPLE 6

Catalyst Q was prepared in the same manner as in Example 5 for preparation of catalyst I, except that 19.06 g of niobium chloride was added.

Catalyst R was prepared in the same manner of preparation of catalyst J, except that the content of rubidium nitrate was 4.44 g and that 6.08 g of ammonium dihydrogen phosphate was added.

The oxidation reaction was conducted in the same procedure as in Example 5.

The catalyst characteristics of catalysts Q, R are shown in Table 1, and the results of oxidation reaction in Table 2.

EXAMPLE 7

Catalysts S, T were prepared in the same manner as in Example 5, except that 18.75 g of antimony trioxide was added, and the oxidation reaction was conducted in the same procedure as in Example 5.

The catalyst characteristics of catalysts S, T are shown in Table 1, and the results of oxidation reaction in Table 2.

EXAMPLE 8

Catalyst U was prepared in the same procedure as in Example 5 for preparing catalyst I, except that the content of cesium sulfate was 6.02 g, and that 19.06 g of niobium chloride and 6.08 g of ammonium dihydrogen phosphate were added.

Catalyst V was prepared in the same manner as in preparation of catalyst J, except that the content of rubidium nitrate was 4.44 g, and that 6.08 g of ammonium dihydrogen phosphate and 18.75 g of antimony trioxide were added.

Thereafter, the oxidation reaction was conducted in the same procedure as in Example 5.

The catalyst characteristics of catalysts U, V are shown in Table 1, and the results of oxidation reaction in Table 2.

EXAMPLE 9

Catalyst W was prepared in the same manner as in Example 5 for preparation of catalyst I, except that 19.06 g of niobium chloride and 18.75 g of antimony trioxide were added.

Catalyst X was prepared in the same manner as in preparation of catalyst J, except that the content of rubidium nitrate was 4.44 g, and that 19.06 g of niobium chloride, 6.08 g of ammonium dihydrogen phosphate, and 18.75 g of antimony trioxide were added.

Thereafter, the oxidation reaction was conducted in the same procedure as in Example 5.

The catalyst characteristics of catalysts W, X are shown in Table 1, and the results of oxidation reaction in Table 2.

Reference 3

Catalyst O (prestage catalyst) was prepared in the same manner as in Example 5 for preparation of catalyst I, except that the content of cesium sulfate was 6.03 g, and that silver nitrate was not added.

Catalyst P (poststage catalyst) was prepared in the same manner as in preparation of catalyst O, except that the content of rubidium nitrate was 4.44 g, and that silver nitrate was not added.

Thereafter, the oxidation reaction was conducted in the same procedure as in Example 5.

The catalyst characteristics of catalysts O, P are shown in Table 1, and the results of oxidation reaction in Table 2.

In these foregoing examples and reference, the oxidation reaction was continued while keeping constant the load to the catalyst, and in the case of oxidation reaction of orthoxylene, the molten salt temperature was set so that the by-product of phthalide was controlled under 0.1 wt. %, while in the case of oxidation reaction of naphthalene, the molten salt temperature was set so that the by-product of naphthoquinone could be controlled under 0.5 wt. %.

TABLE 1

| | Titanium dioxide | Rate of |

TABLE 1-continued

| | Type of catalyst | Catalyst composition (ratio by weight) | | | | | | | | Mean particle size | Specific surface area | fine pore volume |
|---|---|---|---|---|---|---|---|---|---|---|---|---|
| | | $V_2O_5$ | $TiO_2$ | $Nb_2O_5$ | $P_2O_5$ | $Cs_2O$ | $Ag_2O$ | $Sb_2O_3$ | $K_2O$ | | | |
| Example 1 | A | 2 | 98 | 0.5 | 0.2 | 0.25 | 0.2 | 2.0 | — | 0.5 | 22 | 86 |
| | B | 2 | 98 | 0.5 | 0.8 | 0.25 | 0.2 | 2.0 | — | 0.5 | 22 | 87 |
| Example 2 | C | 2 | 98 | 0.5 | 0.2 | 0.25 | 0.2 | 2.0 | — | 0.5 | 22 | 86 |
| | D | 2 | 98 | 0.5 | 0.8 | 0.25 | 0.2 | 2.0 | — | 0.5 | 22 | 87 |
| Example 3 | E | 2 | 98 | 0.5 | 0.2 | 0.25 | 0.2 | 2.0 | — | 0.5 | 22 | 86 |
| | F | 2 | 98 | 0.5 | 0.8 | 0.25 | 0.2 | 2.0 | — | 0.5 | 22 | 87 |
| Reference 1 | K | 2 | 98 | 0.5 | 0.2 | 0.35 | — | 2.0 | — | 0.5 | 22 | 86 |
| | L | 2 | 98 | 0.5 | 0.8 | 0.35 | — | 2.0 | — | 0.5 | 22 | 87 |
| Example 4 | G | 15 | 85 | 0.4 | 0.3 | 0.1 | 1.0 | 2.0 | 0.1 | 0.45 | 33 | 80 |
| | H | 15 | 85 | 0.4 | 0.9 | 0.1 | 1.0 | 2.0 | 0.1 | 0.45 | 33 | 81 |
| Reference 2 | M | 15 | 85 | 0.4 | 0.3 | 0.1 | 2.5 | 2.0 | 0.05 | 0.45 | 33 | 80 |
| | N | 15 | 85 | 0.4 | 0.9 | 0.1 | 2.5 | 2.0 | 0.05 | 0.45 | 33 | 81 |

| | Catalyst | Catalyst composition (ratio by weight) | | | | | | | | | Titanium dioxide | Fine pore volume of 0.15 to 0.45μ |
|---|---|---|---|---|---|---|---|---|---|---|---|---|
| | | $V_2O_5$ | $TiO_2$ | $Nb_2O_5$ | $P_2O_5$ | $Cs_2O$ | $Ag_2O$ | $Sb_2O_3$ | $Rb_2O$ | $Tl_2O$ | | |
| Example 5 | I | 4 | 96 | — | — | 0.2 | 0.1 | — | — | 0.05 | 0.5μ | 85% |
| | J | 4 | 96 | — | — | — | 0.1 | — | 0.1 | — | 22 m²/g | 86% |
| Example 6 | Q | 4 | 96 | 0.5 | — | 0.2 | 0.1 | — | — | 0.05 | 0.5μ | 85% |
| | R | 4 | 96 | — | 0.2 | — | 0.1 | — | 0.15 | — | 22 m²/g | 86% |
| Example 7 | S | 4 | 96 | — | — | 0.2 | 0.1 | 1.0 | — | 0.05 | 0.5μ | 85% |
| | T | 4 | 96 | — | — | — | 0.1 | 1.0 | 0.1 | — | 22 m²/g | 86% |
| Example 8 | U | 4 | 96 | 0.5 | 0.2 | 0.25 | 0.1 | — | — | 0.05 | 0.5μ | 85% |
| | V | 4 | 96 | — | 0.2 | — | 0.1 | 1.0 | 0.15 | — | 22 m²/g | 86% |
| Example 9 | W | 4 | 96 | 0.5 | — | 0.2 | 0.1 | 1.0 | — | 0.05 | 0.5μ | 85% |
| | X | 4 | 96 | 0.5 | 0.2 | — | 0.1 | 1.0 | 0.15 | — | 22 m²/g | 86% |
| Reference 3 | O | 4 | 96 | — | — | 0.25 | — | — | — | 0.05 | 0.5μ | 85% |
| | P | 4 | 96 | — | — | — | — | — | 0.15 | — | 22 m²/g | 86% |

(Note)
Mean particle size: μm
Rate of fine pore volume (rate of total fine pore volume occupied by fine pores with diameter of 0.15 to 0.45 μm to total fine pore volume occupied by fine pores with diameter of 10 μm or less): vol. %

TABLE 2

| Type of catalyst | | Yield of phthalic anhydride (wt. %) | | |
|---|---|---|---|---|
| Pre-stage | Post-stage | Initial (*) | 3 months (*) | 6 months (*) |
| Example 1 | A | B | 114.8 (353) | 115.0 (349) | 115.0 (350) |
| Example 2 | C | D | 114.7 (353) | 115.0 (349) | 115.1 (350) |
| Example 3 | E | F | 114.9 (353) | 115.1 (349) | 115.1 (349) |
| Reference 1 | K | L | 112.5 (353) | 113.0 (349) | 113.0 (350) |
| Example 4 | G | H | 104.5 (363) | 104.7 (358) | 104.8 (357) |
| Reference 2 | M | N | 100.8 (365) | — | — |
| Example 5 | I | J | 113.5 (357) | 113.8 (354) | 113.8 (354) |
| Example 6 | Q | R | 113.6 (356) | 114.0 (352) | 114.1 (351) |
| Example 7 | S | T | 113.8 (358) | 113.9 (355) | 114.0 (354) |
| Example 8 | U | V | 113.8 (358) | 114.2 (353) | 114.0 (353) |
| Example 9 | W | X | 114.0 (355) | 114.3 (352) | 114.1 (352) |
| Reference 3 | O | P | 110.0 (360) | 110.5 (358) | 110.4 (357) |

(*) Molten salt temperature
Examples 1 to 3, reference 1: orthoxylene to phthalic anhydride
Example 4, reference 2: naphthalene to phthalic anhydride
Example 5, reference 3: orthoxylene to phthalic anhydride It is known from the comparison between Examples 1 to 3 and Reference 1, and comparison between Examples 5 TO 9 and Reference 3, that the yield of phthalic anhydride is evidently improved by adding silver, and it is known from the comparison between Example 4 and Reference 2 that there is a limitation to the addition of silver.

As shown in Tables 1 and 2, the catalysts of the invention containing silver improved the yield of phthalic anhydride by about 2% as compared with the catalysts without silver, and the performance of three months and six months later was very stable, and a great economic effect is expected. For example, supposing the present production of phthalic anhydride to be 40,000 tons a year, by the yield increase of 2%, an additional 400 tons of phthalic anhydride will be obtained without increasing the consumption of materials.

What is claimed is:

1. A catalyst for producing phthalic anhydride by vapor phase catalytic oxidation of orthoxylene and/or naphthalene with molecular oxygen or gas containing molecular oxygen, said catalyst having a catalytic active substance comprising 1 to 20 parts by weight of vanadium oxide as $V_2O_5$, 99 to 80 parts by weight of titanium dioxide comprising anatase titanium dioxide having a specific surface area of 10 to 60 m²/g as $TiO_2$, and per 100 parts by weight in total of the above two components, 0.05 to 1.2 parts by weight of at least one element selected from potassium, cesium rubidium and thallium as an oxide, and 0.05 to 2 parts by weight of silver as $Ag_2O$, supported on a heat resistant inorganic carrier.

2. A catalyst for producing phthalic anhydride by vapor phase catalytic oxidation of orthoxylene and/or naphthalene with molecular oxygen or gas containing molecular oxygen, said catalyst having a catalytic active substance comprising 1 to 20 parts by weight of vanadium as $V_2O_5$, 99 to 80 parts by weight titanium dioxide comprising anatase titanium dioxide having a specific surface area of 10 to 60 m²/g as $TiO_2$, and per 100 parts by weight in total of the above two components, 0 to 1 part by weight of niobium as $Nb_2O_5$, 0.05 to 1.2 parts by weight of at least one element selected from potassium, cesium, rubidium and thallium as oxide, 0 to 1.2 parts by weight of phosphorous as $P_2O_5$, 0 to 5 parts by weight of antimony as $Sb_2O_3$, and 0.05 to 2 parts by weight of silver as $Ag_2O$, where the contents of niobium, phosphorous and antimony are not zero at the same time, supported on a heat resistant inorganic carrier.

3. A catalyst for producing phthalic anhydride according to claim 1, wherein the total fine pore volume occupied by fine pores with diameter of 0.15 to 0.45 μm is 50% or more of the total fine pore volume occupied by fine pores with diameter of 10 μm or less, in the catalytic active substance layer supported on the heat resistant inorganic carrier.

* * * * *